(12) United States Patent
Huang et al.

(10) Patent No.: US 8,137,281 B2
(45) Date of Patent: Mar. 20, 2012

(54) STRUCTURE FOR ATTACHING NEEDLE GUIDE TO ULTRASOUND PROBE

(75) Inventors: Shanzhi Huang, Shenzhen (CN); Mengyue Zhang, Shenzhen (CN); Jianfeng Zou, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 690 days.

(21) Appl. No.: 11/512,577

(22) Filed: Aug. 30, 2006

(65) Prior Publication Data

US 2007/0167817 A1    Jul. 19, 2007

(30) Foreign Application Priority Data

Dec. 20, 2005 (CN) .......................... 2005 1 0121068

(51) Int. Cl.
*A61B 17/34* (2006.01)
(52) U.S. Cl. ..................................................... 600/461
(58) Field of Classification Search .................. 600/461
See application file for complete search history.

(56) References Cited

U.S. PATENT DOCUMENTS 5,623,931 A * 4/1997 Wung et al. .................. 600/461
5,758,650 A 6/1998 Miller et al.

FOREIGN PATENT DOCUMENTS

CN       1246041 A    5/2008
* cited by examiner

Primary Examiner — Long V. Le
Assistant Examiner — Helene Bor
(74) Attorney, Agent, or Firm — Kory D. Christensen; Stoel Rives LLP

(57) ABSTRACT

A structure for attaching a needle guide to an ultrasound probe is provided, which includes a probe casing and a needle guide. The probe casing includes a head part provided at a front side of the probe casing and a grasping part provided at a back side of the probe casing and connected with the head part. The needle guide includes a generally "C"-shaped or arcuate clip adapted to be clamped onto the probe casing. The probe casing has opposite outer surfaces each being formed with an outwardly opened and elongated guiding slot extended along a front-back direction. The clip has two clamping arms, each clamping arm having an inner surface opposing to that of the other clamping arm, each inner surface being provided with an elongated clamping protrusion adapted to match and fit with the guiding slot of the probe casing. The clamping protrusions provided on the clamping arm extend in a direction generally perpendicular to the protruding direction of the clamping arms. The structure for attaching a needle guide to an ultrasound probe of the present disclosure is advantageous over the existing structures of the prior art in that the structure is simple, the connection is firm, and the operation is convenient.

26 Claims, 5 Drawing Sheets

STRUCTURE FOR ATTACHING NEEDLE GUIDE TO ULTRASOUND PROBE

FIELD OF THE INVENTION

The present invention relates to an accessory for medical equipment, and especially to an attachment structure for attaching a needle guide to an ultrasound probe.

BACKGROUND ART

Ultrasound probes used in ultrasonic diagnosis apparatus comprise a type of typical ultrasound probes and another type of ultrasound probes equipped with a needle guide for holding a needle such as a puncture needle. In order to conveniently manipulate an ultrasound probe and in the mean while perform needle-puncturing operation in a precise way, people have made corresponding improvements to ultrasound probes and needle guides so that they can be assembled together and detached from each other. For example, U.S. Pat. No. 5,623,931 discloses a technical solution and a concrete structure for assembling and detaching a needle guide with respect to an ultrasound probe. However, this patent, although addresses the technical problem of detachably assembling a needle guide to an ultrasound probe, suffers from the following disadvantages. Specifically, on one hand, this patent provides a complex structure which results in tedious assembling, high manufacturing cost and inconvenient operation, and on the other hand, it requires that the material of the mounting seat for the needle guide has high elasticity and plasticity, which leads to an unstable connection between the needle guide and the ultrasound probe. Other solutions in the prior art for attaching a needle guide to an ultrasound probe also have the shortages of complex structure, unstable connection, inconvenient operation, etc.

SUMMARY OF THE INVENTION

An object of the present invention is to overcome the disadvantages existed in the prior art by providing a simple and cost-effective structure for attaching a needle guide to an ultrasound probe, which structure allows the needle guide to be quickly and firmly attached to the ultrasound probe, as well as allows the ultrasonic inspection and needle punctuation to be performed conveniently.

The technical solutions adopted by the present invention to achieve the above object will be briefly described below.

In one aspect, the present invention provides a structure for attaching a needle guide to an ultrasound probe, comprising a probe casing and a needle guide, wherein the probe casing comprises a head part provided at a front side of the probe casing and a grasping part provided at a back side of the probe casing and connected with the head part, and the needle guide comprises a generally "C"-shaped or arcuate clip adapted to be clamped onto the probe casing, characterized in that, the probe casing has opposite outer surfaces each being formed with an outwardly opened guiding slot or a clamping protrusion, the guiding slot or clamping protrusion having an elongated shape and being extended along a front-back direction; the clip has two clamping arms, each clamping arm having an inner surface opposing to that of the other clamping arm, and each inner surface being provided with a clamping protrusion or a guiding slot having an elongated shape and adapted to match and fit with the corresponding guiding slot or clamping protrusion of the probe casing; and the guiding slots or clamping protrusions provided on the clamping arms extend in a direction generally perpendicular to the protruding direction of the clamping arms;

wherein when it needs to attach the needle guide to the ultrasound probe, the clamping protrusions or guiding slots formed on the inner surfaces of the clamping arms of the clip are aligned with the guiding slots or clamping protrusions formed on the opposite outer surfaces of the probe casing, and then the needle guide is pushed to advance with respect to the ultrasound probe from the back side towards the front side, such that the clamping protrusions insert and fit within the guiding slots respectively, and thus the needle guide is firmly attached to the ultrasound probe; and in a state that the needle guide is attached to the ultrasound probe, by pushing the needle guide with respect to the ultrasound probe from the front side towards the back side, such that the clamping protrusions are moved out from the guiding slots, the needle guide is detached from the ultrasound probe.

Preferably, a bottom surface of each guiding slot is formed with a positioning convex portion, and a top surface of the corresponding clamping protrusion, which opposes to the bottom surface of the guiding slot, is formed with a positioning concave portion, wherein in a state that the needle guide is attached to the ultrasound probe, the positioning convex portions snap into the positioning concave portions respectively so as to fix the needle guide to the ultrasound probe.

Preferably, each positioning convex portion extends transversely to the opposing walls defining the corresponding guiding slot, i.e., in a direction generally perpendicular to the longitudinal direction of the guiding slot, and the positioning concave portion to be snapped by the positioning convex portion is adapted to match with the positioning convex portion.

Preferably, in the case that the guiding slots are formed on the opposite outer surfaces of the probe casing, each guiding slot is formed cross a joint line between the curved surfaces of the head part and the grasping part of the probe casing, and the guiding slot is opened from a initial portion on the grasping part and ended with a end portion on the head part.

Preferably, the width of each guiding slot decreases from its initial portion towards its end portion, and the corresponding clamping protrusion is adapted to have a wedge shape to match with the guiding slot.

Preferably, a top inner surface of the clip is formed with a supplementary guiding recess or block generally parallel to the clamping protrusions or guiding slots of the clip, and the probe casing is formed with a supplementary guiding block or recess which matches with the supplementary guiding recess or block of the clip, wherein when the needle guide is being attached to the ultrasound probe, the supplementary guiding block slidably inserts into the supplementary guiding recess.

Preferably, the clip is made of a plastic material or a similar material having certain elasticity, thus an elastic clamping force can be created between a top surface of the supplementary guiding block and a bottom surface of the supplementary guiding recess.

Preferably, the supplementary guiding block and the supplementary guiding recess each have a shape in a cross-section perpendicular to its extension direction selected from the group consisted of rectangular, square, semi-circular, part-circular, trapezoidal, triangular, and combinations of them.

Preferably, a leading end of the supplementary guiding block to be firstly inserted into the supplementary guiding recess is formed with a transitional curved shape to facilitate the inserting of the supplementary guiding block into the supplementary guiding recess.

Preferably, the guiding slots or clamping protrusions of the probe casing are symmetrically provided on the opposite outer surfaces of the probe casing, and the clamping protrusions or guiding slots of the clip are symmetrically provided on the inner surfaces of the clamping arms of the clip.

Preferably, the clip is made of a plastic material or a similar material having certain elasticity, thus an elastic clamping force can be created between an inner wedging surface of each clamping protrusion and a facing wall of the corresponding guiding slot.

Preferably, the guiding slots and the clamping protrusions each have a shape in a cross-section perpendicular to its extension direction configured so as to, in the fitting state of them, prevent the clamping protrusions from occasionally coming out from the guiding slots.

Preferably, the guiding slot has a dovetail, trapezoidal or rectangular shape in its cross-section.

Preferably, each guiding slot is formed with a transitional curved shape at its initial portion to facilitate the inserting of the corresponding clamping protrusion into the guiding slot.

Another object of the present invention is to provide a medical needle guide which can be used cooperatively with an ultrasound probe.

To this end, the present invention provides a medical needle guide, to be used with an ultrasound probe, comprising a generally "C"-shaped or arcuate clip to be clamped onto a probe casing of the ultrasound probe, and a needle carrying and guiding member removably mounted to the clip, characterized in that the clip has two clamping arms, each clamping arm having an inner surface opposing to that of the other clamping arm, and each inner surface being provided with a clamping protrusion or a guiding slot having an elongated shape and being adapted to match and fit with an outwardly opened guiding slot or a clamping protrusion provided on an outer surface of the probe casing and extending along a front-back direction of the probe casing, and the guiding slots or clamping protrusions provided on the clamping arms extend in a direction generally perpendicular to the protruding direction of the clamping arms;

Preferably, the clamping protrusions or guiding slots of the clip are each formed with a positioning concave portion or a positioning convex portion for engaging with a corresponding positioning convex portion or a positioning concave portion formed on the corresponding guiding slot or clamping protrusion of the probe casing.

Preferably, a top inner surface of the clip is formed with a supplementary guiding recess or block generally parallel to the clamping protrusion or guiding slot of the clip for fitting with a corresponding supplementary guiding block or recess formed on the probe casing.

The structure for attaching a needle guide to an ultrasound probe of the present invention is advantageous over the existing structures of the prior art in that, first, the structure is simple and allows conveniently attaching and detaching the needle guide to and from the ultrasound probe, and second, a stable and firm connection can be obtained between the needle guide and the ultrasound probe.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

An embodiment of the structure for attaching a needle guide to an ultrasound probe according to the present invention will now be described with reference to the figures, wherein like numbers represent like parts.

Figure 1:
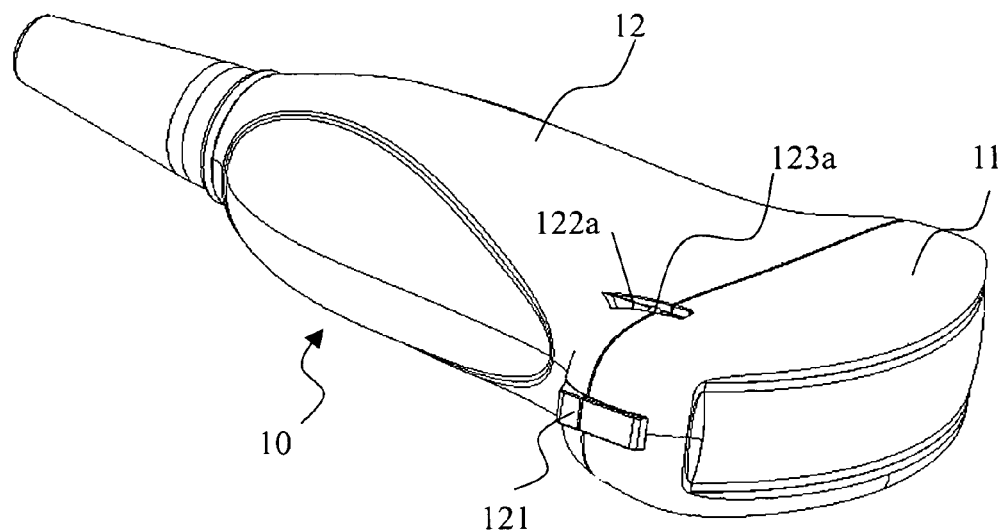
FIG. 1 a schematic perspective view of the ultrasound probe of the present invention.
Figure 2:
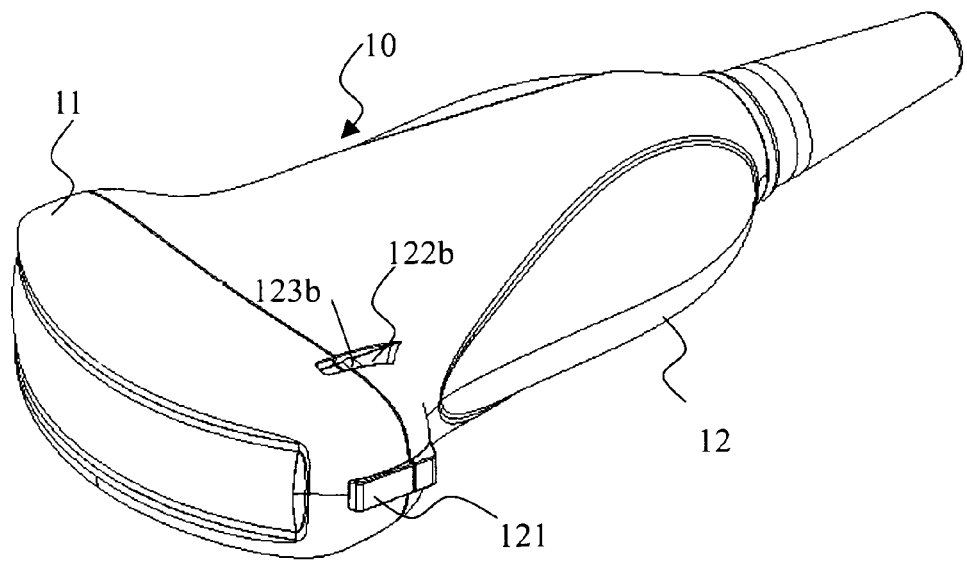
FIG. 2 a schematic perspective view of the ultrasound probe taken from another side.
Figure 3:
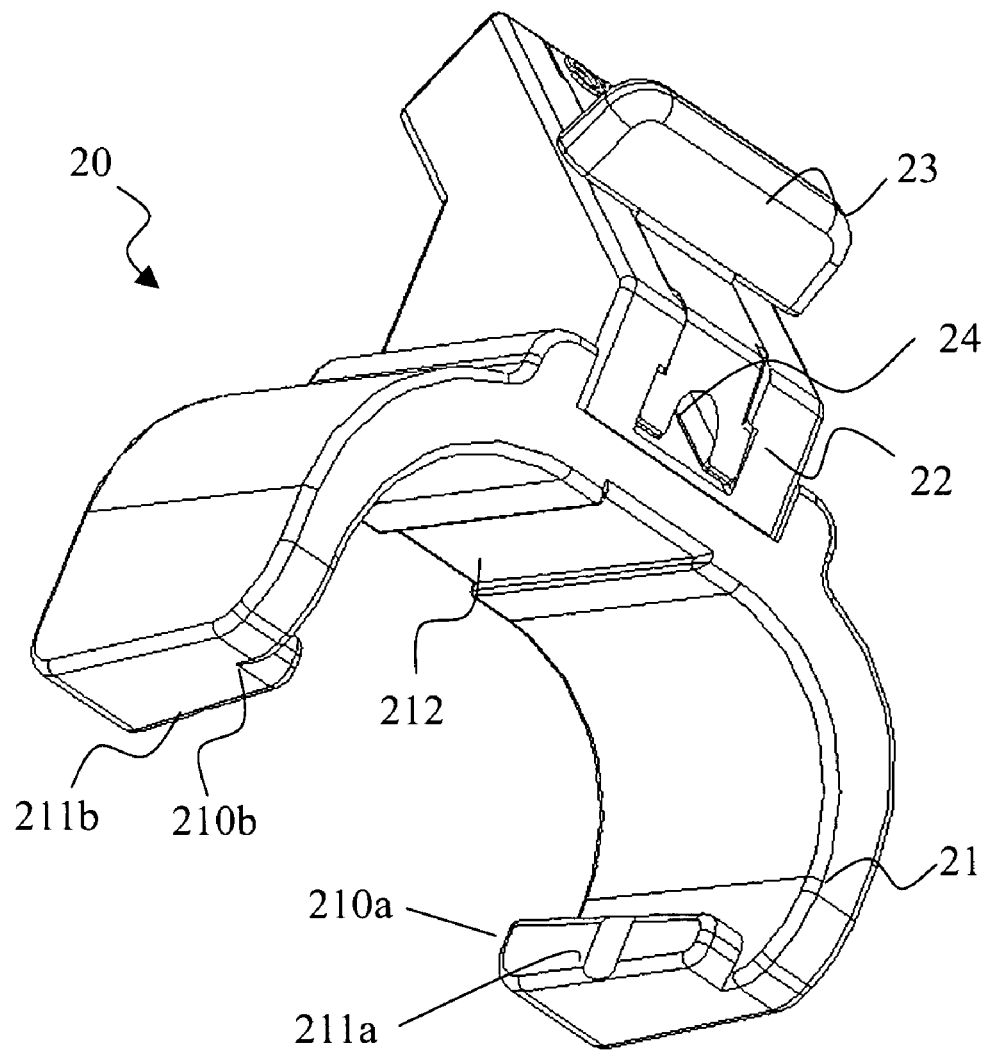
FIG. 3 a schematic perspective view of the needle guide of the present invention.
Figure 6:
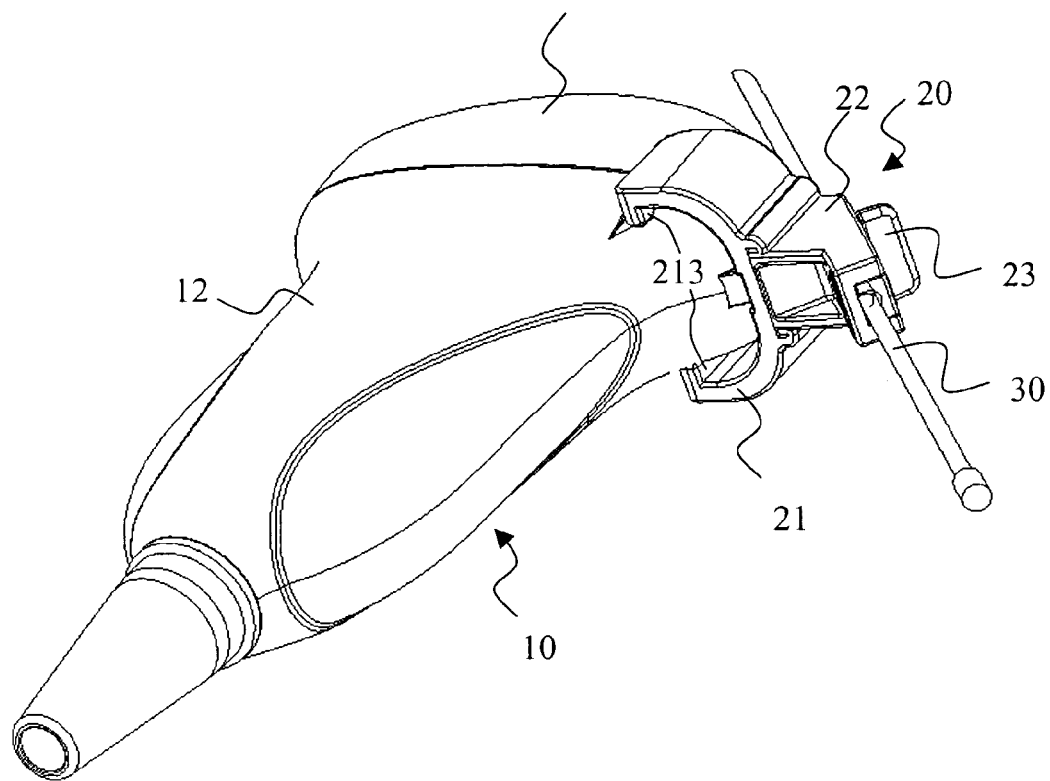
FIG. 6 a schematic perspective view showing the needle guide attached to the ultrasound probe.

As shown in FIG. 6, a structure for attaching a needle guide to an ultrasound probe according to the present invention comprises a probe casing 10 and a needle guide 20. The probe casing 10 comprises a head part 11 provided at a front side of the probe casing and a grasping part 12 provided at a back side of the probe casing and connected with the head part 11. Herein the term "front side" refers to the side proximal to the person inspected by the ultrasonic diagnosis apparatus (or the patient), while the term "back side" refers to the side distal to the person inspected by the ultrasonic diagnosis apparatus (or the patient). The needle guide 20 comprises a generally "C"-shaped or arcuate clip 21 for clamping onto the probe casing. As shown in FIGS. 1 and 2, the probe casing 10 has opposite outer surfaces each of which being formed with a corresponding outwardly opened guiding slot 122a or 122b. As shown in FIG. 3, the clip 21 has two clamping arms, and the opposing inner surfaces of the clamping arms are each formed with an clamping protrusion 211a or 211b configured to match and fit with the corresponding guiding slot 122a or 122b.

The guiding slots 122a and 122b provided on the probe casing 10 and the corresponding clamping protrusions 210a and 210b provided on the inner surfaces of the clamping arms of the clip 21, which as stated above match and fit with each other, can be reversed in location with respect to each other. That is to say, although not shown, the probe casing 10 may be formed with two clamping protrusions, and meanwhile the inner surfaces of the clamping arms of the clip 21 may be formed with two guiding slots matching and fitting with the corresponding clamping protrusions.

As shown in the figures, each of the guiding slots and the clamping protrusions has a generally elongated shape extending from the back side to the front side. That is to say, the longitudinal direction of each of the guiding slots and the clamping protrusions is directed along a front-back direction.

Figure 4:
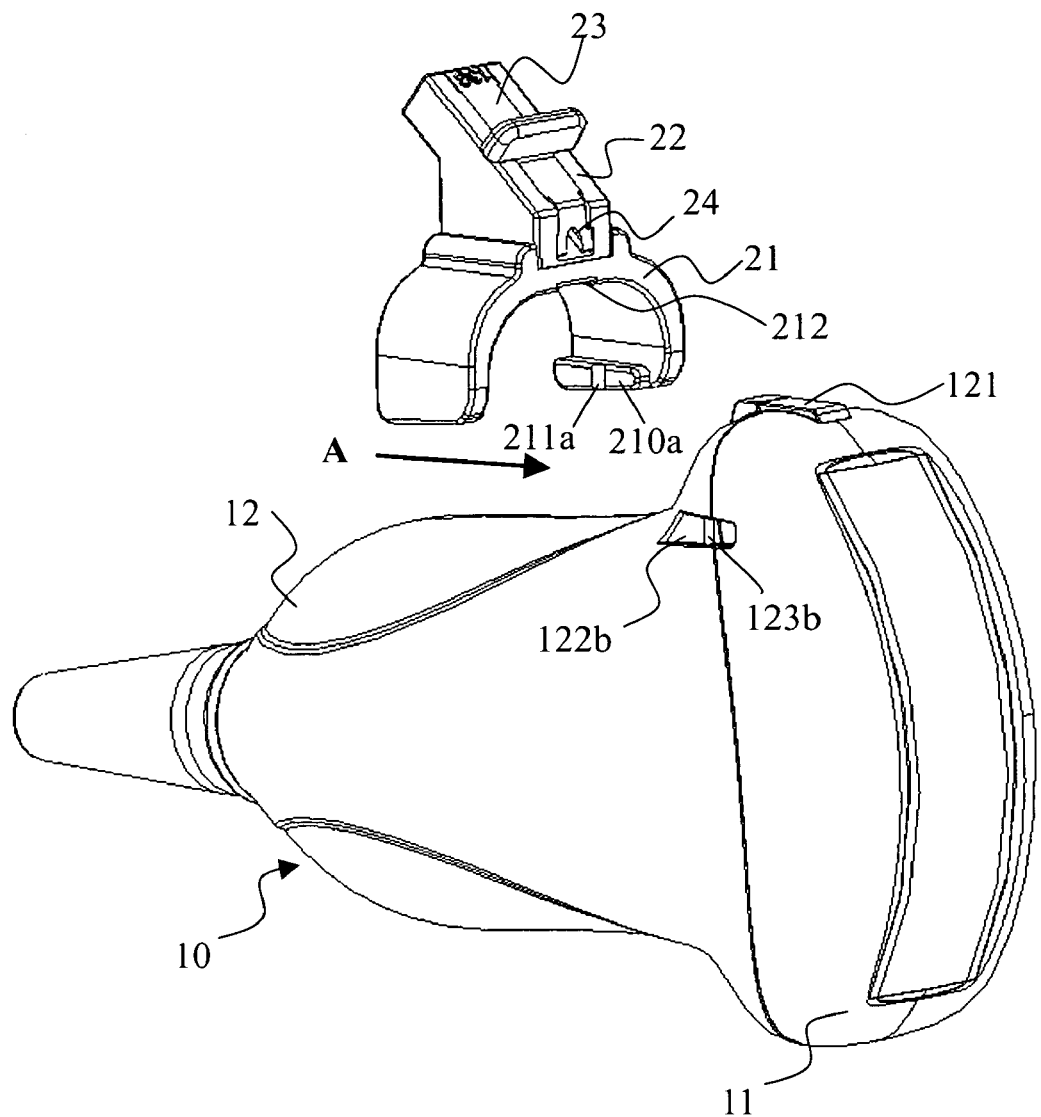
FIG. 4 a schematic perspective view showing the force applying direction in an attaching step of the needle guide of the present invention.

As shown in FIGS. 1, 2 and 4, in the case that the guiding slots 122a and 122b are provided on the outer surfaces of the probe casing 10, the two guiding slots 122a and 122b are each formed cross a joint line between the curved surfaces of the head part 11 and the grasping part 12 of the probe casing 10, and the guiding slots 122a and 122b extend from the back side of the ultrasound probe to its front side respectively. In other words, each guiding slot is opened from an initial portion on the grasping part 12 and ended with an end portion on the head part 11. In this way, the outer profile of a traditional ultrasound probe is effectively taken into consideration. Meanwhile, by providing the guiding slots 122a and 122b proximal to a transitional portion at the curved joint line between the curved surfaces of the head part 11 and the grasping part 12 of the probe casing 10, the outer appearance of the probe casing 10 will not be affected, while the attachment of the needle guide 20 to the probe casing of the ultrasound probe can be facilitated. The width of each guiding slot 122a or 122b decreases from its initial portion towards its end portion, and the corresponding clamping protrusion 210a or 210b is adapted to have a wedge shape to match with the guiding slot, so that the clamping protrusions 210a and 210b can be more smoothly pushed into or pulled out from the guiding slots 122a and 122b.

In order to facilitate the assembling and the detaching of the needle guide and the ultrasound probe, while maintain the outer appearance of the whole product, the two guiding slots 122a and 122b (or clamping protrusions) are symmetrically provided on the opposite outer surfaces of the probe casing 10, and correspondingly, the two clamping protrusions 210a and 210b (or guiding slots) are symmetrically provided on the inner surfaces of the clamping arms of the clip 21.

In order to further enhance the firm connection between the needle guide 20 and the probe casing 10 and the precise assembling and positioning between them, each guiding slot 122a and 122b provided on the probe casing 10 is formed with a positioning convex portion 123a or 123b, as shown in FIGS. 1 and 2, and each clamping protrusion 210a and 210b provided on the inner surface of the clamping arms of the clip 21 is formed with a positioning concave portion 211a or 211b corresponding to and being adapted to be fit with the positioning convex portion 123a or 123b (see FIG. 3). The positioning convex portions 123a and 123b may have various shapes or configuring manners, among which a preferred configuring manner is that the positioning convex portion 123a or 123b extends transversely to the opposing walls defining the guiding slot 122a or 122b, i.e., along a direction generally perpendicular to the longitudinal direction of the guiding slot 122a or 122b, while the positioning concave portion 211a or 211b formed on the clamping protrusion 210a or 210b is adapted to match and fit with the positioning convex portion 123a or 123b.

Furthermore, as shown in FIG. 3, a top inner surface of the clip 21 is formed with a supplementary guiding recess 212, while the probe casing 10 is formed with a supplementary guiding block 121 (see FIGS. 1 and 2) adapted to match and fit with the supplementary guiding recess 212. As a result, the firm connection between the needle guide 20 and the probe casing 10 is additionally enhanced. The locations of supplementary guiding recess 212 and the supplementary guiding block 121 can be reversed with respect to each other. That is to say, the top inner surface of the clip 21 may be formed with a supplementary guiding block, while the probe casing 10 may be formed with a supplementary guiding recess matching and fitting with the supplementary guiding block.

As shown in FIGS. 3, 4 and 6, the clip 21 is made of a plastic material or a similar material having certain elasticity. By forming the clip 21 with such material, the two clamping arms of the clip is flexible or can be deflected to some extend. Meanwhile, each of the guiding slots 122a and 122b provided on the opposite outer surfaces of the probe casing 10 may be formed with a transitional curved shape at its initial portion to facilitate the inserting of the clamping protrusions 210a and 210b into the guiding slots 122a and 122b. Moreover, a leading end of the supplementary guiding block 121 to be inserted into the supplementary guiding recess 212 is also formed with a transitional curved shape to facilitate the inserting of the supplementary guiding block 121 into the supplementary guiding recess 212.

Figure 5:
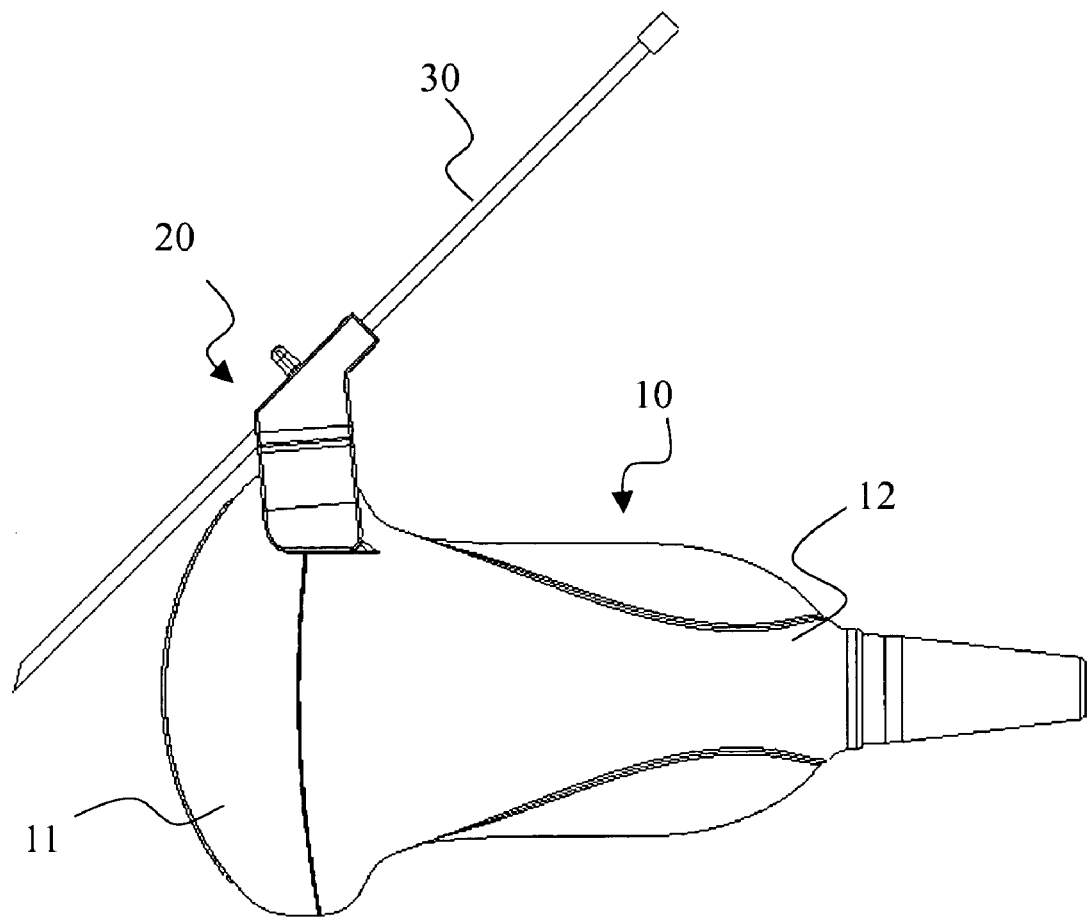
FIG. 5 is a schematic front view showing the needle guide attached to the ultrasound probe.

As shown in FIG. 4, when it needs to attach the needle guide 20 to the probe casing 10, the two clamping protrusions 210a and 210b are aligned to the initial ends of the guiding slots 122a and 122b respectively, then the needle guide 20 is pushed to advance along a direction indicated by the arrow A shown in FIG. 4 from the grasping part 12 side to the head part 11 side. When the needle guide 20 is pushed into position, the two clamping protrusions 210a and 210b fit closely within the corresponding guiding slots 122a and 122b respectively, the positioning convex portions 123a and 123b snap tightly into the positioning concave portions 211a and 211b respectively, and the supplementary guiding block 121 fits within the supplementary guiding recess 212. Since the clip 21 is made of a plastic material or a similar material having certain elasticity, when the needle guide 20 is assembled with the probe casing 10, an inner wedging surface 213 (see FIG. 6) of each of the two clamping protrusions 210a and 210b snugly abuts a facing wall of the corresponding guiding slot 122a or 122b, while a bottom surface of the supplementary guiding recess 212 snugly abuts a top surface of the supplementary guiding block 121, and thus elastic clamping forces are generated at these abutting interfaces, so the needle guide 20 is attached to the probe casing 10 in a very stable and firm manner (see FIGS. 5 and 6). In a state that the needle guide 20 is attached to the probe casing 10, owing to the holding forces provided by the engagement between the positioning convex portions 123a and 123b and the positioning concave portions 211a and 211b, the occasional detachment of the clamping protrusions 210a and 210b from the guiding slots 122a and 122b can be prevented; that is, a certain force applied to the needle guide 20 in a direction reverse to the arrow A to overcome all the elastic clamping forces and the holding forces is essential for retracting the needle guide 20 from the probe casing towards the back side.

With reference to FIG. 3, the medical needle guide 20 of the present invention for used with an ultrasound probe comprises the generally "C"-shaped or arcuate clip 21 to be clamped onto the probe casing, and a needle carrying and guiding member removably mounted to the clip. The needle carrying and guiding member comprises an angled block 22 and a guiding block 23. The angled block 22 is removably clamped in a chute formed near the outer surface of the clip 21, and a needle insertion hole 24 to be inserted through by a needle 30 such as a puncture needle is defined between the guiding block 23 and the angled block 22. The inner surfaces of the clamping arms of the clip 21 are formed with the clamping protrusions 210a and 210b to be clamped onto the probe casing, and the clamping protrusions are formed with the positioning concave portions 211a and 211b respectively. As described above, the clamping protrusions 210a and 210b may be substituted by guiding slots, and in this case, the positioning concave portions 211a and 211b are substituted by positioning convex portions. Moreover, the top inner surface of the clip 21 is formed with the supplementary guiding recess 212 or the supplementary guiding block.

As shown in FIG. 4, in the state that the needle guide 20 (without mounting the guiding block 23 thereon) is attached to the probe casing 10, the probe casing 10 is manipulated by an operator to contact with and scan the body of the patient. The operator can observe the scanning ultrasonic images obtained from the ultrasound probe and determine the location of a puncturing target such as an unconditioned focus. Once the location of the unconditioned focus is determined, the operator can select a suitable needle 30 and a corresponding guiding block 23 according to concrete requirement, and mount and fix the selected guiding block 23 to the angled block 22 of the needle guide 20. Then the operator can move the needle 30 up and down within the needle insertion hole 24 delimited between the guiding block 23 and the angled block 22 (the needle 30 is not shown in FIG. 4, but can be seen from FIGS. 5 and 6). Once the operator confirms that the needle 30 has already reached to the unconditioned focus, the guiding block 23 can be removed from the angled block 22 fixed to the needle guide 20, and the probe casing 10 with the needle guide 20 (without the guiding block 23) can be moved away from another side. Thereafter, the operator may use only the needle 30 to draw out target tissues from the body of the patient or infuse medical agents into the body of the patient through the needle 30.

When the needle guide 20 should be detached from the probe casing 10, it needs only to push the clip 21 outwardly from the probe casing 10 in a direction reverse to the arrow A in FIG. 4 and then the detachment operation can be fulfilled.

What is claimed is:

1. An ultrasonic probe system comprising:
    a probe casing, wherein the probe casing comprises a head part provided at a front side of the probe casing and a grasping part provided at a back side of the probe casing and connected with the head part, wherein the probe casing comprises opposite outer surfaces, wherein at least one of the outer surfaces is formed with a guiding slot or a clamping protrusion, and wherein the probe casing comprises a major axis extending from the head part to the grasping part; and
    a needle guide comprising an arcuate clip configured to be clamped onto the probe casing, wherein the clip comprises two clamping arms, wherein each clamping arm comprises an inner surface, wherein at least one of the inner surfaces comprises a clamping protrusion or a guiding slot, wherein the clamping protrusion or guiding slot of the needle guide is configured to match and fit with the corresponding guiding slot or clamping protrusion of the probe casing, wherein the guiding slot comprises an open end configured to receive the clamping protrusion and guide the clamping protrusion into the guiding slot, wherein the guiding slot comprises a terminal end opposite the open end such that the guiding slot extends from the open end to the terminal end, wherein the clamping protrusion comprises a leading end and a terminal end opposite the leading end such that the clamping protrusion extends from the leading end to the terminal end, wherein the guiding slot is configured to initially receive the leading end of the clamping protrusion at the open end of the guiding slot so as to guide the leading end through the guiding slot from the open end of the guiding slot until the leading end is adjacent to the terminal end of the guiding slot, wherein a bottom surface of the guiding slot is formed with a positioning convex portion, and a top surface of the corresponding clamping protrusion is formed with a positioning concave portion, wherein the positioning convex portion is configured to snap into the positioning concave portion so as to fix the needle guide to the ultrasound probe, and wherein the guiding slot and the clamping protrusion are configured such that the needle guide can be connected with the probe casing by moving the needle guide in a direction substantially parallel to the major axis of the probe casing.

2. The system of claim 1, wherein the guiding slot is elongated and extends in a longitudinal direction, and wherein the positioning convex portion extends in a direction substantially perpendicular to the longitudinal direction of the guiding slot.

3. The system of claim 1, wherein guiding slots are formed on the opposite outer surfaces of the probe casing, wherein each guiding slot is formed across a joint line between surfaces of the head part and the grasping part of the probe casing, and wherein the guiding slot is opened from a initial portion on the grasping part and ended with a end portion on the head part.

4. The system of claim 3, wherein the width of each guiding slot decreases from its initial portion towards its end portion, and wherein the corresponding clamping protrusion of each guiding slot has a wedge shape at least approximately matching the shape of the guiding slot.

5. The system of claim 1, wherein a top inner surface of the clip is formed with a supplementary guiding recess or block generally parallel to the clamping protrusion or guiding slot of the clip, wherein the probe casing is formed with a supplementary guiding block or recess that matches with the supplementary guiding recess or block of the clip, and wherein the supplementary guiding block and supplementary guiding recess are configured such that the supplementary guiding block is slidably received within the supplementary guiding recess.

6. The system of claim 5, wherein the clip is at least partially flexible such that an elastic clamping force is generated between a top surface of the supplementary guiding block and a bottom surface of the supplementary guiding recess while the supplementary guiding block is engaged within the supplementary guiding recess.

7. The system of claim 5, wherein the supplementary guiding block and the supplementary guiding recess each have a shape in a cross-section perpendicular to its extension direction selected from the group consisted of rectangular, square, semi-circular, arch, trapezoidal, triangular, and combinations thereof.

8. The system of claim 5, wherein a leading end of the supplementary guiding block configured to be firstly inserted into the supplementary guiding recess is formed with a transitional curved shape to facilitate the inserting of the supplementary guiding block into the supplementary guiding recess.

9. The system of claim 1, wherein the guiding slots or clamping protrusions of the probe casing are symmetrically positioned on the opposite outer surfaces of the probe casing, and wherein the clamping protrusions or guiding slots of the clip are symmetrically positioned on the inner surfaces of the clamping arms of the clip.

10. The system of claim 1, wherein the clip is at least partially flexible such that an elastic clamping force is generated between an inner wedging surface of each clamping protrusion and a wall of the corresponding guiding slot.

11. The system of claim 1, wherein the guiding slot and the clamping protrusion each have a cross-sectional shape configured so as to maintain a friction fit between the guiding slot and the clamping protrusion.

12. The system of claim 11, wherein the guiding slot has a cross-sectional shape of at least one of a dovetail, trapezoidal, and rectangular shape.

13. The system of claim 1, wherein each guiding slot is formed with a transitional curved shape to facilitate inserting the corresponding clamping protrusion into the guiding slot.

14. The system of claim 1, wherein the guiding slot is formed in an elongated shape and wherein the guiding slot extends along a front-back direction.

15. The system of claim 1, wherein the guiding slot or clamping protrusion positioned on at least one of the clamping arms extends in a direction substantially perpendicular to a protruding direction of the at least one clamping arm.

16. The system of claim 1, wherein the clamping protrusion or guiding slot formed on the inner surface of the clamping arm of the clip is configured to be aligned with the guiding slot or clamping protrusion of the probe casing, and wherein the needle guide is configured to be pushed to advance the needle guide with respect to the ultrasound probe from the back side towards the front side, such that the clamping protrusion inserts and fits within the guiding slot to firmly attach the needle guide to the ultrasound probe.

17. The system of claim 1, wherein the needle guide is detachable from the ultrasound probe by pushing the needle guide with respect to the ultrasound probe from the front side towards the back side, such that the clamping protrusion is removed from the guiding slot.

18. The system of claim 1, wherein both of the outer surfaces comprise a guiding slot or a clamping protrusion, and wherein both of the inner surfaces comprise a corresponding clamping protrusion or guiding slot.

19. The system of claim 1, wherein the terminal end of the guiding slot comprises a closed end, wherein the closed end is configured to prevent a clamping protrusion from entering or exiting the guiding slot at the closed end such that the clamping protrusion is only slidably received within the guiding slot from the open end and can only be slidably removed from the guiding slot at the open end.

20. A medical needle guide, for use with an ultrasound probe, comprising:

a clip configured to be clamped onto a probe casing of an ultrasound probe, wherein the probe casing comprises a major axis extending from a head part provided at a front side of the probe casing to a grasping part provided at a back side of the probe casing and connected with the head part, wherein the clip comprises two clamping arms, each clamping arm having an inner surface opposing that of the other clamping arm, wherein both inner surfaces comprise a clamping protrusion or a guiding slot having an elongated shape and being configured to match and fit with a corresponding guiding slot or clamping protrusion on the ultrasound probe, wherein each of the guiding slots comprise an open end configured to receive a clamping protrusion and guide the clamping protrusion into the guiding slot, wherein each of the guiding slots comprise a terminal end opposite the open end such that the guiding slot extends from the open end to the terminal end, wherein each of the clamping protrusions comprise a leading end and a terminal end opposite the leading end such that the clamping protrusion extends from the leading end to the terminal end, and wherein each of the guiding slots are configured to initially receive the leading end of a clamping protrusion at the open end of the guiding slot so as to guide the leading end through the guiding slot from the open end of the guiding slot until the leading end is adjacent to the terminal end of the guiding slot, wherein a bottom surface of the guiding slot is formed with a positioning convex portion, and a top surface of the corresponding clamping protrusion is formed with a positioning concave portion, wherein the positioning convex portion is configured to snap into the positioning concave portion so as to fix the clip to the probe casing, and wherein the guiding slot and the clamping protrusion are configured such that the needle guide can be connected with the probe casing by moving the needle guide in a direction substantially parallel to the major axis of the probe casing; and a needle carrying and guiding member mounted to the clip.

21. The needle guide of claim 20, wherein a top inner surface of the clip is formed with a supplementary guiding recess or supplementary guiding block that is configured for fitting with a corresponding supplementary guiding block or supplementary guiding recess formed on the probe.

22. The needle guide of claim 20, wherein the needle carrying and guiding member is removably mounted to the clip.

23. The needle guide of claim 20, wherein the clip is substantially in the shape of a "C".

24. The needle guide of claim 20, wherein the guiding slots have an elongated shape and extend along a front-back direction of the probe casing.

25. The needle guide of claim 20, wherein the guiding slots or clamping protrusions positioned on the clamping arms extend in a direction substantially perpendicular to a protruding direction of the clamping arms.

26. The needle guide of claim 20, wherein the terminal end of at least one of the guiding slots comprises a closed end, wherein the closed end is configured to prevent a clamping protrusion from entering or exiting the guiding slot at the closed end such that the clamping protrusion is only slidably received within the guiding slot from the open end and can only be slidably removed from the guiding slot at the open end.

* * * * *